United States Patent [19]

Lohmann et al.

[11] 4,301,075
[45] Nov. 17, 1981

[54] N-SUBSTITUTED IMIDES AND BIS-IMIDES

[75] Inventors: Dieter Lohmann, Muttenz; Martin Roth, Marly; Marcus Baumann, Basel, all of Switzerland

[73] Assignee: Ciba-Geigy Corporation, Ardsley, N.Y.

[21] Appl. No.: 67,863

[22] Filed: Aug. 20, 1979

[30] Foreign Application Priority Data

Aug. 30, 1978 [CH] Switzerland ............... 9153/78

[51] Int. Cl.$^3$ .................................. C07D 207/24
[52] U.S. Cl. ............... 260/326.5 FM; 260/245.4; 260/326 N; 260/326.5; 260/326 C; 260/326.26; 260/326.5 B; 544/357; 546/16
[58] Field of Search ............... 260/326.5 FM

[56] References Cited

U.S. PATENT DOCUMENTS

| | | | |
|---|---|---|---|
| 2,676,179 | 4/1954 | Prill | 260/326.5 FM |
| 3,755,354 | 8/1973 | Holub et al. | 260/326 E |
| 3,966,531 | 6/1976 | Bargain | 260/326 E |
| 4,130,564 | 12/1978 | Haug et al. | 260/326.5 FM |

OTHER PUBLICATIONS

P. Tawney, Chem. Abstr. 59: P9815e, (1963).
U.S. Rubber Co., Chem. Abstr. 57: 11358b, (1962).
Uchiyama et al., Chem. Abstr. 78: 15554t, (1973).
Block et al., Chem. Abstr. 78: 72734a, (1973).
H. Yocum et al., Functional Monomers, Marcel Dekkar, N.Y., vol. 2, pp. 235–238, (1974).
B. Lipinski, Defazet, 28, 207, (1974).
F. Horsch, Kunststoffe, 55, 909, (1965).
Hackh's Chemical Dictionary, Fourth Ed., p. 27, McGraw-Hill, N.Y., 1979.

*Primary Examiner*—Donald G. Daus
*Assistant Examiner*—M. C. Eakin
*Attorney, Agent, or Firm*—Luther A. R. Hall

[57] ABSTRACT

Compounds of the formulae I or II

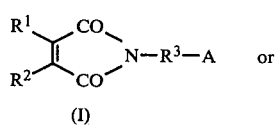

(I)

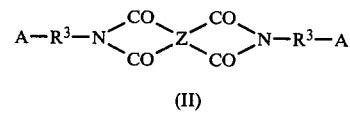

(II)

and processes for their preparation are described. In the above formulae, Z is a tetravalent aliphatic radical, which can be interrupted by hetero-atoms, or a substituted or unsubstituted tetravalent cycloaliphatic radical, which can contain hetero-atoms and/or can be fused to a benzene ring, A is $-C(R^4)=C(R^5)(R^6)$ or $-C\equiv C-R^5$, especially $-CH=CH_2$, $R^1$ and $R^2$ independently of one another are H, methyl, phenyl, $-CN$ or Cl, or together are trimethylene, tetramethylene,

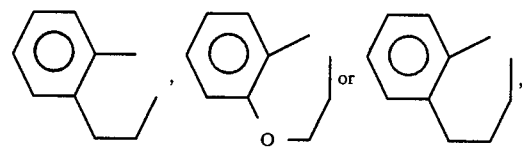

$R^3$ is a direct bond, $C_{1-8}$ alkylene, cyclohexylene, phenylene or $-CH_2$-phenylene with the $-CH_2$ group bonded to the N atom, $R^4$ and $R^6$ independently of one another are H, methyl or ethyl and $R^5$ is H or $C_{1-9}$ alkyl. The compounds of the formula I and II are valuable intermediates for the preparation of silicon-modified adhesion promoters.

5 Claims, No Drawings

N-SUBSTITUTED IMIDES AND BIS-IMIDES

The present invention relates to novel N-substituted imides and bis-imides and processes for their preparation. The novel imides and bis-imides are valuable intermediates which are suitable, for example, for the preparation of silicon-modified adhesion promoters, for example between inorganic solids and organic resins.

It is known from the literature that diverse silanes, such as vinyl trichlorosilane, vinyl-tris-(2-methoxyethoxy)-silane, γ-aminopropyltriethoxysilane and [N-(2-aminoethyl)-3-aminopropyl]-trimethoxysilane, can be used as adhesion promoters for diverse applications, for example for the production of glass fibre-reinforced plastics, especially laminate sheets for electrical applications, and for sealing compositions, lacquers and adhesives [cf., for example, Defazet, 28, 207–211 (1974) and Kunststoffe, 55, 909–912 (1965), U.S. Pat. No. 3,755,354 and German Offenlegungsschrift No. 2,504,791].

However, the properties of the products obtained with these known adhesion promotors leave something to be desired in some respects. The products are in particular to be regarded as very unfavourable in respect of one or more of the following 3 properties: absorption of water, thermo-oxidative stability and dielectric characteristics. The N-substituted imides and bis-imides according to the invention are suitable for the preparation of silicon-modified adhesion promoters, with which the above disadvantages can be avoided.

The novel imides and bis-imides have the formula

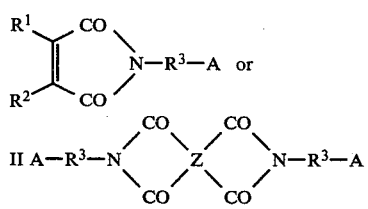

in which Z is a tetravalent aliphatic radical, which can be interrupted by hetero-atoms, or a substituted or unsubstituted tetravalent cycloaliphatic radical, which con contain hetero-atoms and/or can be fused with a benzene ring, the carbonyl groups preferably being bonded to different C atoms of Z, $R^1$ and $R^2$ independently of one another are hydrogen, methyl, phenyl, —CN or chlorine, or $R^1$ and $R^2$ together are trimethylene, tetramethylene,

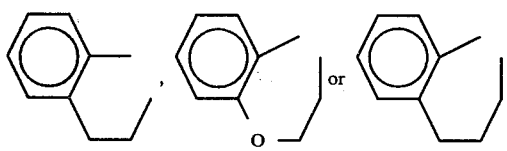

$R^3$ is a direct bond, alkylene having 1–8 C atoms, cyclohexylene, phenylene, or —CH$_2$-phenylene with the —CH$_2$ group bonded to the N atom. A is a group

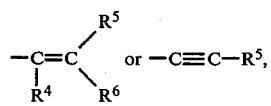

$R^4$ and $R^6$ independently of one another are hydrogen, methyl or ethyl and $R^5$ is hydrogen or alkyl having 1–9 C atoms, with the proviso that $R^3$ in formula I is alkylene having 2–8 C atoms, cyclohexylene or —CH$_2$-phenylene if $R^1$ and $R^2$ are hydrogen or chlorine or one of $R^1$ and $R^2$ is methyl and A is —CH=CH$_2$, and is alkylene having 1–8 C atoms, cyclohexylene, phenylene or —CH$_2$-phenylene if $R^1$ and $R^2$ together are tetramethylene and A is —CH=CH$_2$.

Tetravalent aliphatic radicals Z can be straight-chain or branched and/or interrupted by one or more heteroatoms, in particular N atoms. In particular, these radicals are alkanetetrayl groups having 2–8 C atoms, which can be interrupted by N atoms, such as the groups

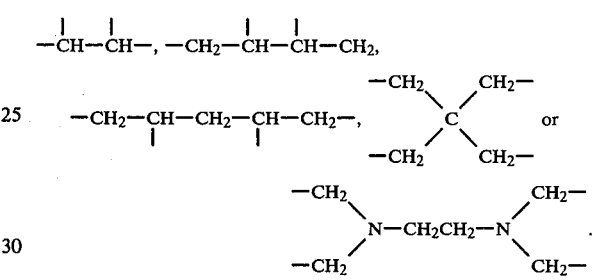

A cycloaliphatic radical Z according to the definition is in particular a radical of the formula

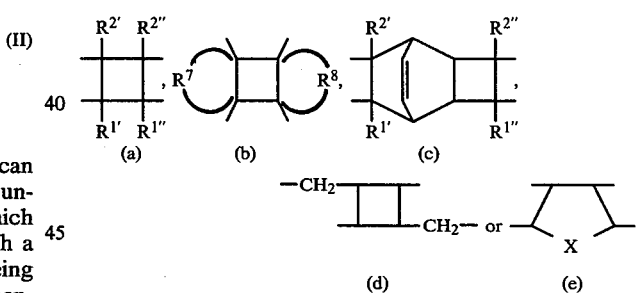

in which X is —CH$_2$— or —O—, $R^{1'}$, $R^{1''}$, $R^{2'}$ and $R^{2''}$ independently of one another are hydrogen, methyl, phenyl, —CN or chlorine and $R^7$ and $R^8$ independently of one another are alkylene having 3–4 C atoms, which can be branched and can be interrupted by a heteroatom, especially —O—, and/or fused with a benzene ring. Preferably, Z is one of the abovementioned radicals (a), (b), (c), (d) or (e) or a radical of the formula

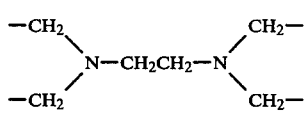

in which radical $R^{1'}$, $R^{1''}$, $R^{2'}$ and $R^{2''}$ and X are as defined and $R^7$ and $R^8$ are each trimethylene, tetramethylene,

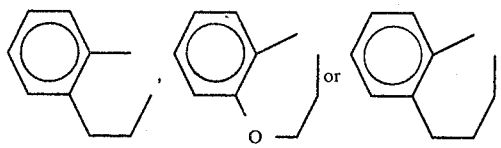

Particularly preferred groupings Z are those of the formulae (a), (b) and (e) indicated above, in which X is as defined and in particular is —O—, $R^{1'}$, $R^{2'}$, $R^{1''}$ and $R^{2''}$ independently of one another are hydrogen or methyl and $R^7$ and $R^8$ are each tetramethylene.

Alkylene groups $R^3$ can be straight-chain or branched. If A is a group

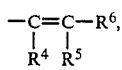

alkylene groups $R^3$ are preferably straight-chain. If A is a group —C≡C—$R^5$, $R^3$ is preferably methylene or a branched alkylene group, such as —C(CH$_3$)$_2$— or —C(C$_2$H$_5$)$_2$. Examples of such alkylene groups $R^3$ are: the methylene, 1,2-ethylene, 1,3-, 1,2- and 2,2,-propylene, 2,2-dimethyl-1,3-propylene, 2,2-pentylene, tetramethylene, hexamethylene and octamethylene groups.

A cyclohexylene grouup $R^3$ is in particular the 1,4-cyclohexylene group or, if A=—C≡C—$R^5$, also the 1,1-cyclohexylene group.

A phenylene or —CH$_2$-phenylene group $R^3$ is in particular the 1,2- or 1,4-phenylene group or the

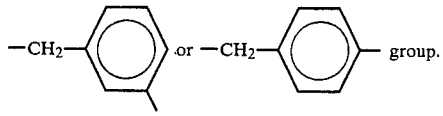 group.

Alkyl groups $R^5$ can be straight-chain or branched. Straight-chain alkyl groups $R^5$ are preferred. Examples of alkyl groups $R^5$ according to the definition are: the methyl, ethyl, n-propyl, isopropyl, n-butyl, sec.-butyl, n-pentyl, n-hexyl, n-heptyl and n-nonyl groups.

Preferred compounds of the formula I are those in which A is

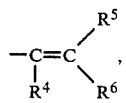

$R^1$ and $R^2$ are each methyl, $R^3$ is a direct bond, methylene,

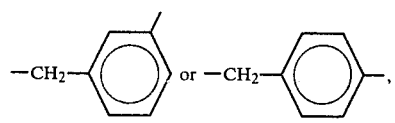

$R^4$ and $R^6$ independently of one another are hydrogen or methyl and $R^5$ is hydrogen, methyl or n-octyl, or in which A is as defined, $R^1$ and $R^2$ together are tetramethylene, $R^3$ is methylene,

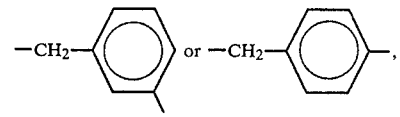

$R^4$ and $R^6$ independently of one another are hydrogen or methyl and $R^5$ is hydrogen or methyl; and also compounds of the formula I in which A is —C≡C—$R^5$, $R^1$ and $R^2$ are each methyl, $R^3$ is methylene, 2,2-propylene, 2,2-pentylene or 1,1-cyclohexylene and $R^5$ is hydrogen or methyl.

Preferred compounds of the formula II are those in which A is —C($R^4$)=C($R^5$)($R^6$), Z is a grouping (a), (b) or (e), X is —CH$_2$— and especially —O—, $R^{1'}$, $R^{2'}$, $R^{1''}$ and $R^{2''}$ independently of one another are hydrogen or methyl, $R^3$ is a direct bond, methylene,

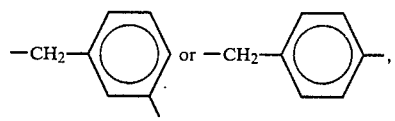

$R^4$, $R^5$ and $R^6$ independently of one another are hydrogen or methyl and $R^7$ and $R^8$ are each tetramethylene, and also compounds of the formula II in which A is —C≡C—$R^5$, Z, X, $R^{1'}$, $R^{2'}$, $R^{1''}$, $R^{2''}$, $R^7$ and $R^8$ are as defined above, $R^3$ is methylene, 2,2-propylene, 2,2-pentylene or 1,1-cyclohexylene and $R^5$ is hydrogen or methyl.

Very particularly preferred compounds of the formulae I and II are those in which A is —CH=CH$_2$, $R^1$ and $R^2$ are each methyl, $R^3$ is a direct bond or methylene and Z is a grouping (a), in which $R^{1'}$, $R^{2'}$, $R^{1''}$ and $R^{2''}$ are each methyl.

Compounds of the formula I or II in which $R^3$ is alkylene having 1–8 C atoms, cyclohexylene, phenylene or —CH$_2$-phenylene with the —CH$_2$ group bonded to the N atom, and what has been stated under the formulae I and II applies in respect of $R^1$, $R^2$, A and Z, can be prepared, for example, by (a) reacting a compound of the formula III

with a compound of the formula IV

H$_2$N—$R^{3'}$—A  (IV)

or (b) reacting a compound of the formula V

with a compound of the formula IV, and cyclising the amidocarboxylic acid of the formula VIa or VIb which is formed,

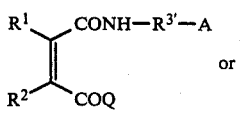 (VIa)

or

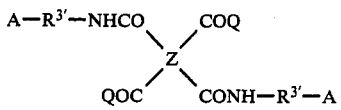 (VIb)

in wich formulae III, IV, V, VIa and VIb, what has been stated under formulae I and II applies in respect of A, R$^1$, R$^2$ and Z, R$^{3'}$ is alkylene having 1-8 C atoms, cyclohexylene, phenylene or —CH$_2$-phenylene with the —CH$_2$ group bonded to the N atom, Q$_1$ is —OH, chlorine, alkoxy having 1-6 C atoms or phenoxy and Q$_2$ is alkoxy having 1-6 C atoms or phenoxy, or Q$_1$ and Q$_2$, in pairs, form the grouping —O—, Q is —OH, alkoxy having 1-6 C atoms or phenoxy and the groupings —COQ$_1$ and —COQ$_2$ in formula V and also the groupings —COQ and the carboxamide groups in formula VIb are preferably bonded to different C atoms of Z.

Alkoxy groups Q, Q$_1$ and Q$_2$ can be straight-chain or branched, but are preferably straight-chain and have 1 or 2 C atoms. Depending on the nature of the reactants and on the reaction conditions, the compounds of the formula III which are used are preferably the corresponding anhydrides, acid chlorides or half-esters. Preferred compounds of the formula V are the dianhydrides.

The amine of the formula IV is employed in at least the stoichiometric amount; however, a slight excess of amine of the formula IV can also be used.

The reaction of the compounds of the formulae III and V with the amine of the formula IV and also the subsequent cyclisation of the amidocarboxylic acids are preferably carried out in an inert organic solvent, such as N,N-dimethylformamide, N,N-dimethylacetamide, benzene, toluene, xylene, n-hexane or cloroform. However, the reaction can also be carried out without the additional use of an organic solvent. The reaction temperatures for the reaction of the compounds of the formula III or V with the amines of the formula IV are in general between about 20° and 180° C. The cyclisation can be effected by azeotropic removal of the water of reaction formed, by the addition of conventional dehydrating agents, such as acetic anhydride or propionic anhydride, if desired in a mixture with tertiary amines, such as triethylamine or pyridine, or sodium acetate, or, alternatively, in the presence of water-binding agents, such as molecular sieves.

Compounds of the formula I or II in which R$^3$ is a direct bond, alkylene having 1-8 C atoms, cyclohexylene or —CH$_2$-phenylene with the —CH$_2$ group bonded to the N atom, and what has been stated under the formulae I and II applies in respect of R$^1$, R$^2$, A and Z, can also be prepared by reacting a compound of the formula VIIa or VIIb

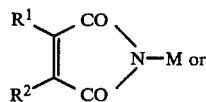 (VIIa)

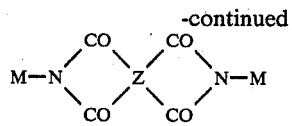 (VIIb)

with a compound of the formula VIII

X$_1$—R$^{3''}$—A    (VIII)

in which formulae VIIa, VIIb and VIII what has been stated under the formulae I and II applies in respect of A, R$^1$, R$^2$ and Z, M is an alkali metal, X$_1$ is a halogen atom and R$^{3''}$ is a direct bond, alkylene having 1-8 C atoms, cyclohexylene or —C$_2$-phenylene with the —CH$_2$ group bonded to the N atom. M is preferably sodium or potassium and X$_1$ is preferably chlorine or bromine. The reaction can be carried out without a solvent or in the presence of an organic solvent, such as N,N-dimethylformamide, N,N-dimethylacetamide, methanol or ethanol. The compound of the formula VIII is employed in at least the stoichiometric amount; however, a slight excess of the compound of the formula VIII can also be used.

Compounds of the formula I or II in which A is a group —C≡C—R$^5$ can, if desired, be converted by catalytic hydrogenation, for example in the presence of so-called Lindlar catalysts, to compounds of the formula I or II in which A is a group —CH═CH—R$^5$.

Compounds of the formula I in which R$^3$ is a direct bond and A is —CH═CH$_2$ can also be obtained according to methods known per se, by the elimination of water from the corresponding N-β-hydroxyethylimides, by the elimination of hydrogen halides from the corresponding N-β-halogenoethylamides, by thermal decomposition (pyrolysis) of corresponding N-β-acetoxyethylimides, by reaction of the imides with vinyl acetate or by adding on acetylene.

Finally, compounds of the formula II in which Z is a grouping (a), (b) or (c), R$^{1'}$, R$^{2'}$, R$^{1''}$ and R$^{2''}$ independentlyof one another are hydrogen, methyl, phenyl, —CN or chlorine and R$^7$ and R$^8$ independently of one another are trimethylene, tetramethylene,

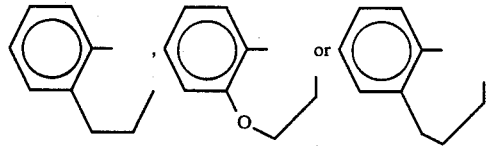

can also be obtained by irradiating a compound of the formula I with UV light, advantageously at temperatures between about 5° and 120° C. and if desired in the presence of sensitisers and/or benzene. If benzene is also used, a Diels-Alder reaction can also take place at the same time as the photo-addition, and compounds of the formula II in which Z is a grouping (c) are formed. Sensitisers which can be used are compounds which are known per se, such as thioxanthones, which can be halogenated, benzophenone or acetophenone. The dimerisation is advantageously carried out in an inert organic solvent, such as acetone or dioxan.

The starting materials of the formulae III, IV, V, VIIa, VIIb and VIII are known or can be prepared by methods known per se. Salts of the formulae VIIa and VIIb can be obtained, for example, by reacting the corresponding imides or bis-imides with alkali metal hydroxides or alkali metal alcoholates, in particular sodium hydroxide and potassium hydroxide, sodium methylate or potassium methylate.

The compounds of the formulae I and II are valuable intermediates which are suitable, for example, for the preparation of silicon-modified adhesion promoters. Such adhesion promoters can be prepared by reacting a compound of the formula I or II with a silane of the formula IX

     (IX)

to give a compound of the formula Xa or Xb

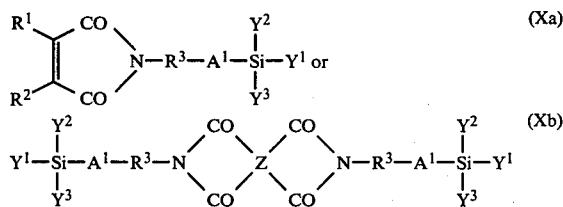

in which $A^1$ is a group

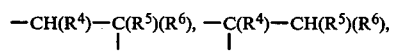

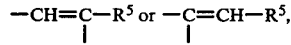

what has been stated under the formulae I and II applies in respect of $R^1$ to $R^6$ and Z, $Y^1$ and $Y^2$ independently of one another are methyl, ethyl, phenyl, vinyl or a group $Y^3$, and $Y^3$ is —Cl, $C_1$-$C_{10}$ alkoxy, $C_5$-$C_8$ cyclo alkoxy or phenoxy.

Alkoxy groups $Y^1$, $Y^2$ and $Y^3$ can be straight-chain or branched, but preferably are straight-chain and have 1–6 and especially 1–3 C atoms. preferably, $Y^1$ is methyl and $Y^2$ and $Y^3$ independently of one another are alkoxy having 1–3 C atoms, cyclohexyloxy or phenoxy. Particularly preferred compounds of the formulae Xa and Xb are those in which $R^1$ to $R^6$ and Z have the preferred meaning defined above, $Y^1$ is methyl and $Y^2$ and $Y^3$ are each n-propoxy.

The addition reaction of the silane of the formula IX with the compounds of the formula I or II can be carried out in a manner known per se, in the presence of catalysts, such as platinum, rhodium and palladium, or oxides, salts or complexes thereof, or hexachloroplatinic acid, and, if desired, in the presence of inert organic solvents, for example toluene, benzene, xylenes or dioxan.

The compounds of the formulae Xa and Xb are valuable adhesion promoters, especially between inorganic solids and organic resins, and are suitable for a large number of applications in the adhesives industry and in the lacquer-processing and plastics-processing industries.

Examples of some fields of application are: for improvement of the adhesion of specific sealing compositions, for example polysulfides, polyurethanes and polyacrylates, on diverse substrates, such as glass, aluminium and ceramics; for coating mineral fillers in order to improve the mechanical properties of the products prepared therewith, for example in the case of the sand-filled masks and cores used in the casting industry, mineral-filled cable mixtures or other mineral-filled plastics, for example filled thermosetting plastics, such as quartz-filled epoxide resins and filled unsaturated polyesters, filled thermoplastics, such as polyamide 6,6 and polyethylene terephthalate, and filled elastomers, such as natural rubber and synthetic rubbers; and for adhesives, adhesive compositions and epoxide, polyacrylate, polyurethane and vinyl chloride copolymer lacquers. However, the said compounds are suitable in particularfor the prepartion of reinforced plastics, especially glass fibre-reinforced plastics, especially composite materials, such as laminates for electrical applications, in order to improve the adhesion between the substrate or the matrix and the plastic applied thereto. The substrate can be in any form per se, for example in the form of fibres, woven fabrics or nonwovens, and preferably consists of glass, or alternatively of mineral materials, such as quartz, rock wool, asbestos or mica, or metallic fibres and foils. Suitable plastics for the preparation of such laminates are, for example, acrylates and polyester, epoxide, silicone, melamine, phenol and furan resins; further suitable plastics are also polyamides and polyamidoacids or polyimides, but especially polymers crosslinkable via C=C double bonds, such as unsaturated polyesters and homo- and co-polymers containing maleimidyl or nadicimidyl groups, their precursors or mixtures with other polymers.

Compared with silicon-containing adhesion promoters previously known, the adhesion promoters of the formulae Xa and Xb are distinguished, in particular, by a lower volatility and by an increased stability to high temperatures, better stability to boiling water and good dielectric properties of the products prepared therefrom. Moreover, the adhesion promoters of the formulae Xa and Xb are readily soluble in organic solvents, have low sensitivity to hydrolysis and are stable on storage.

As can be seen from the description given above, compounds of the formula I are also starting materials for the preparation of compounds of the formula II. They can furthermore be used to prepare photocrosslinkable polymers with imidyl groups in side positions, by polymerising them, if desired in the presence of ethylenically unsaturated comonomers, such as alkyl acrylates or alkyl methacrylates, methyl vinyl ether, styrene or maleic anhydride. Compounds of the formula II can also be used as curing agents for polymers having C=C double bonds, for example unsaturated polyesters or bis-maleimides, or as crosslinking agents in polymerization reactions, for example in the polymerisation of styrene, acrylic derivatives and similar monomers.

EXAMPLE 1

(Process Ia)

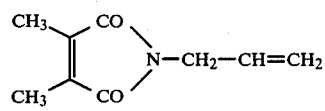

A solution of 57 g (1 mol) of allylamine in 200 ml of toluene is added dropwise to a mixture of 126 g (1 mol) of 2,3-dimethylmaleic anhydride and 500 ml of toluene, with stirring. After the exothermic reaction has subsided, the mixture is refluxed under a water separator until the calculated amount of water has been separated off. The reaction solution is dried over magnesium sulfate and filtered and the filtrate is freed from the solvent in vacuo. The residual oil is distilled under a high vacuum. Boiling point 125°–130° C./2666.6 Pa; yield 154.2 g=93.5% of theory.

EXAMPLE 2

(Process Ib)

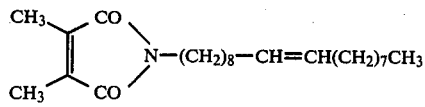

12.6 g (0.1 mol) of 2,3-dimethylmaleic anhydride and 26.7 g (0.1 mol) of oleylamine are mixed together and heated at 180° C. (bath temperature) for one hour. The mixture is then dried in vacuo at about 100°–120° C. The liquid imide thus obtained can be employed for further reactions without additional purification. Yield: 36.5 g=97% of theory; mass spectrum: M+: 375.

Analysis for $C_{24}H_{41}O_2N$ (molecular weight 375.6): Calculated: C 76.7%; H 11.0%; N 3.7%. Found: C 76.5%; H 11.0%; N 3.7%.

EXAMPLE 3

(Process II)

Analogously to Example 2, 126 g (1 1 mol) of 2,3-dimethylmaleic anhydride and 61 g (1 mol) of ethanolamine are reacted to give 150 g of N(2-hydroxyethyl)-2,3-dimethylmaleimide (boiling point 110° C. under 13.3 Pa; yield 89% of theory). The N(2-hydroxyethyl)-2,3-dimethylmaleimide is mixed with 181.5 g (1.78 mols) of acetic anhydride and 3 drops of concentrated sulfuric acid and the mixture is refluxed for one hour in an oil bath heated to 160° C. The acetic acid formed and the acetic anhydride are then distilled off in vacuo. Fractionation of the residue under a high vacuum yields 179 g of N(2-acetoxyethyl)-2,3-dimethylmaleimide (boiling point 104° C./6.66 Pa; yield 95% of theory). The N(2-acetoxyethyl)-2,3-dimethylmaleimide is introduced dropwise, under nitrogen, in the course of 75 minutes into a glass column which is filled with Raschig rings and is heated to 550° C. The pyrolysis products are collected at the lower end of the glass column in a cooled receiver. The yellow oil obtained is taken up in diethyl ether and treated with aqueous sodium bicarbonate solution in order to remove the acetic acid. After drying the organic phase over sodium sulfate, the solvent is removed in vacuo and the product is distilled under a high vacuum. In addition to 39.3 g of unconverted starting material, 84.7 g of (N-vinyl)-2,3-dimethylmaleimide are obtained in the form of a yellowish oil; boiling point 58°–60° C./53.33 Pa; yield: 85% of theory, based on converted starting material.

EXAMPLES 4–9

Further compounds of the formulae

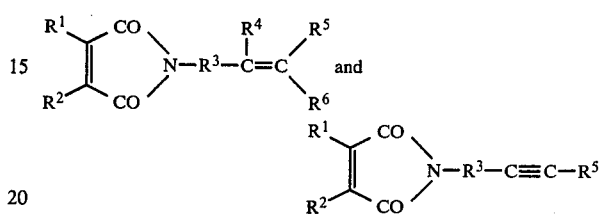

which have been prepared by the processes described in Examples 1 and 2 are listed in Table I below.

TABLE I

| Example No. | Process | $R^1$ | $R^2$ | $R^3$ | $R^4$ | $R^5$ | $R^6$ | Boiling point °C./Pa | Elementary analysis % calculated/% found | |
|---|---|---|---|---|---|---|---|---|---|---|
| 4 | Ia | phenyl | methyl | methylene | H | H | H | 118–120 0.133 | C 73.9/74.1; N 6.1/6.3 | H 5.7/5.9; |
| 5 | Ib | methyl | methyl | 2,2-propylene | — | H | — | 125–128 2666.6 | C 69.1/69.3; N 7.3/7.3 | H 6.9/7.0; |
| 6 | Ib | methyl | methyl | 2,2-pentylene | — | H | — | 136–140 2666.6 | C 71.2/71.1; N 6.4/6.4 | H 7.8/8.0; |
| 7 | Ib | methyl | methyl | 1,1-cyclo-hexylene | — | H | — | 96–100 13.33 | C 72.7/72.8; N 6.1/6.5 | H 7.4/7.4; |
| 8 | Ia | ⌬ (naphthyl) | | —CH₂— | H | H | H | melting point 67–69 | C 75.3/75.5; N 5.8/6.1 | H 5.4/5.6; |
| 9 | Ia | phenyl | H | —CH₂— | H | H | H | melting point 152–154 | C 73.2/72.8; N 6.6/6.9 | H 5.2/5.5; |

EXAMPLE 10

Process III

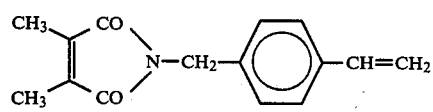

38.1 g (0.25 mol) of 4-chloromethyl-styrene are added slowly dropwise to a suspension of 29.4 g (0.2 mol) of sodium 2,3-dimethylmaleimide [prepared from 2,3-dimethylmaleimide and sodium methylate] in 100 ml of dry N,N-dimethylformamide. After the exothermic reaction has subsided, the reaction mixture is stirred for 1 hour at 60° C. and, after cooling, 500 ml of distilled water are added. The aqueous mixture is extracted with 200 ml of diethyl ether and after drying the organic phase over sodium sulfate the diethyl ether is distilled off. The resulting yellow, viscous oil is freed from solvent residues at 50° C./0.133 Pa. Yield 27.4 g (=57% of theory).

Analysis for $C_{15}H_{15}NO_2$: Calculated: C 74.67%; H 6.27%; N 5.81%. Found: C 74.6%; H 6.5%; N 5.8%.

EXAMPLE 11

Analogously to Example 10, 16.3 g (0.1 mol) of potassium 2,3-dimethylmaleimide [prepared from 2,3-dimethylmaleimide and potassium methylate in methanol] and 16.3 g (0.1 mol) of 6-bromo-1-hexene are reacted. The reaction mixture is heated at 80° C. for 2.5 hours and worked up as described. The resulting N-[hex-5-enyl]-2,3-dimethylmaleimide is a yellow viscous oil. Yield 15 g=72% of theory.

Analysis for $C_{12}H_{17}NO_2$: Calculated: C 69.54%; H 8.26%; N 6.75%. Found: C 69.2%; H 8.4%; N 7.0%.

EXAMPLE 12

Process A

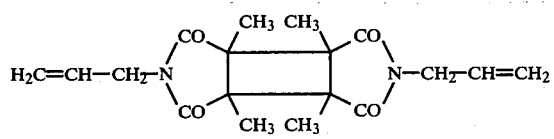

A well-stirred mixture of 20 g (0.121 mol) of (N-allyl)-2,3-dimethylmaleimide [prepared according to Example 1] and 80 ml of dry acetone is irradiated under nitrogen in a water-cooled radiation apparatus (150 watt mercury high-pressure lamp). After 24 hours, the product which has precipitated is filtered off and the filtrate is irradiated for a further 24 hours, after which the product which has precipitated is again filtered off. The resulting solid product is recrystallised from cyclohexane. After evaporation of the filtrate, the residue is purified by chromatography on silica gel using chloroform as the solvent. Melting point 202° C.; yield 10.1 g=50.5% of theory; molecular weight caluclated=33, molecular weight found=337.

EXAMPLE 13

Process B

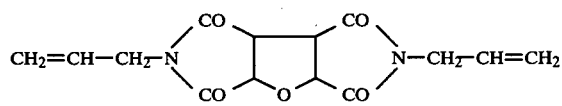

A solution of 57.1 g (1 mol) of allylamine is added dropwise at 20°–40° C. to a mixture of 106 g (0.5 mol) of tetrahydrofuran-tetracarboxylic acid dianhydride and 300 ml of anhydrous N,N-dimethylformamide. After the exothermic reaction has subsided, the reaction mixture is stirred for a further 10 hours at 25° C. A mixture of 500 ml of acetic anhydride and 161 ml of pyridine is then added and the reaction mixture is kept at 30° C. for 3 hours. The clear reaction solution is then evaporated in vacuo and the residue is introduced into 2 liters of distilled water. The resulting fine suspension is filtered and the material on the filter is washed with three times 100 ml of distilled water. The resulting product is dried, first over phosphorus pentoxide and then under a high vacuum. After recrystallisation from toluene, a finely crystalline white powder is obtained. Yield 107 g=84% of theory; melting point 162° C.

EXAMPLE 14

Process C

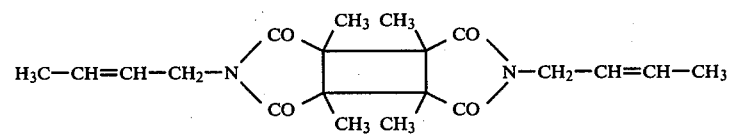

10.9 g (0.080 mol) of crotyl bromide are added slowly to a suspension of 11.8 g (0.040 mol) of N,N'-bis-(sodium)-1,2,3,4-tetramethyl-cyclobutane-1,2,3,4-tetracarboxylic acid diimide [prepared from 1,2,3,4-tetramethyl-cyclobutane-1,2,3,4-tetracarboxylic acid diimide and sodium methylate in N,N-dimethylacetamide] in 300 ml of dry methanol. After the addition is complete, the reaction mixture is heated at 50°–60° C. for 2 hours and one liter of distilled water is then added at 20°–25° C. The product is extracted with methylene chloride. The resulting solution is dried over sodium sulfate and filtered and the filtrate is freed from the solvent in vacuo. The resulting crystalline white product is purified by recrystallisation from diethyl ether. Yield 8.6 g=60% of theory; melting point 194°–199° C.

Elementary analysis for $C_{20}H_{26}N_2O_4$: Calculated: C 67.02%; H 7.31%; N 7.82%. Found: C 66.6%; H 7.2%; N 8.0%.

EXAMPLES 15-19

The compounds of the formula

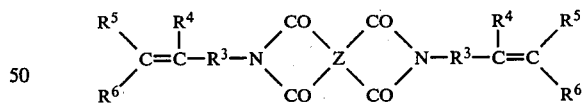

listed in Table II below were prepared by a procedure analogous to that described in Example 12 and 13, thioxanthone in a concentration of 0.5% by weight being added as a sensitiser in some cases. + indicates that thioxanthone is also used.

TABLE II

| Example No. | Process | $R^3$ | Z | Thio-xanthone | $R^4$ | $R^5$ | $R^6$ | Melting point °C. | $M_{calculated}$ $M_{found}$ |
|---|---|---|---|---|---|---|---|---|---|
| 15 | A | direct bond | CH3 CH3 / CH3 CH3 | + | H | H | H | >200 (decomposition) | 302 325 |

TABLE II-continued

| Example No. | Process | R³ | Z | | | | Thioxanthone | R⁴ | R⁵ | R⁶ | Melting point °C. | $M_{calculated}$ $M_{found}$ |
|---|---|---|---|---|---|---|---|---|---|---|---|---|
| 16 | A | —CH₂— | H H / H H | | | | + | H | H | H | 136 | 274 / 291 |
| 17 | A | —CH₂— | H₅C₆ CH₃ / CH₃ C₆H₅ | | | | | H | H | H | 78–82 | 454 / 487 |
| 18 | A | —CH₂— | Cl Cl / Cl Cl | | | | + | H | H | H | | 412 |
| 19 | B | —CH₂— | —CH₂\ /CH₂— N—CH₂—CH₂—N —CH₂/ \CH₂— | | | | | H | H | H | 77–82 | 334 / 338 |

$M$ = molecular weight

USE EXAMPLE I

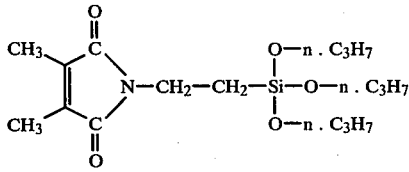

A mixture of 30.2 g (0.2 mol) of the (N-vinyl)-2,3-dimethylmaleimide prepared according to Example 3, 100 ml of dry xylene and 1 ml of a 0.02 molar solution of hexachoroplatinic (IV) acid in n-propanol is warmed to 120° C. under nitrogen. At this temperature, a solution of 43.5 g (0.21 mol) of tri-n-propoxysilane and 1 ml of 0.02 molar H₂PtCl₆ (in n-propanol) in 50 ml of xylene is added slowly dropwise at such a rate that the reaction temperature is 120°–130° C. The reaction mixture is then heated at 140° C. for a further 1 hour, the solvent is removed in vacuo and the product is distilled under a high vacuum. Boiling point 105° C./0.133 Pa. Yield 42 g=59% of theory.

USE EXAMPLE II

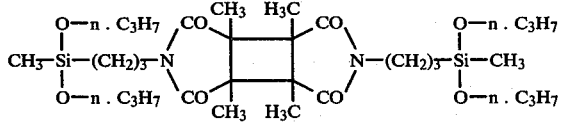

A mixture of 3.1 g (0.094 mol) of the N,N'-bis-(allyl)-1,2,3,4-tetramethyl-cyclobutane-1,2,3,4-tetracarboxylic acid diimide prepared according to Example 12 and 0.5 ml of a 0.02 molar solution of hexachloroplatinic(IV) acid in n-propanol and 10 ml of dry xylene is heated to 110° C. under nitrogen. At this temperature, a mixture of 3.0 g (0.188 mol) of methyl-di-n-propoxysilane, 0.5 ml of 0.02 molar catalyst solution and 5 ml of xylene is added slowly dropwise at such a rate that the reaction temperature is 110°–120° C. The reaction mixture is then heated at 120° C. for a further 1 hour and the solvent is removed in vacuo. After recrystallisation from petroleum ether, the product is obtained in the form of a finely crystalline, white powder; melting point 62°–64° C. Yield 3.9 g=64% of theory.

(a) Impregnation of glass fabric:

Glass fabric, so-called E-glass, which has a weight of 280 g/m² and satin weave and has previously been desized by the action of heat to a residual size content of about 0.1% by weight, is impregnated with 2% solutions of the above adhesion promoters I and II and of known adhesion promoters. The adhesion promoter solutions are applied by the dipping process at an impregnation speed of 0.5 m/minute and are then dried for 20 minutes at 180° C. in a circulating air oven. Prepregs are obtained which have an adhesion promoter content of about 0.09 to 0.11% by weight, based on the glass fibre. The adhesion promoters (finishes) used are:

(1) No adhesion promoter
(2) Vinyl-tris-(2-methoxyethoxy)-silane ("Silan A 172" from Union Carbide); 2% solution in N,N-dimethylformamide (DMF)
(3) γ-Aminopropyl-triethoxysilane ("Silan A 1100" from Union Carbide); 2% solution in DMF
(4) Chromium chloride-methacrylate complex ("Volan-A" from DuPont); 2% solution in DMF
(5) The product according to Example 1 of U.S. Pat. No. 3,755,354 (γ-maleimidopropyltriethoxysilane); 2% solution in DMF
(6) The diimide according to Example 4 of U.S. Pat. No. 3,901,913; 2% solution in DMF
(7) The diimide according to Example 2a of German Offenlegungsschrift No. 2,504,791; 2% solution in DMF.
(I) Adhesion promoter according to Use Example I; 2% solution in DMF
(II) Adhesion promoter according to Use Example II; 2% solution in DMF.

(b) Production of copper-coated laminate sheets:

1.0 mol of N,N'-4,4'-diphenylmethane-bis-maleimide is dissolved at 100° C. in 500 g of furfuryl alcohol and the solution is cooled to 25° C. 0.4 mol of 4,4'-diaminodiphenylmethane are dissolved at 25° C. in 200 g of 2-methoxyethanol (methylene glycol monomethyl ether). The two solutions are combined and mixed well. Using this solution, the glass fabric finished in accordance with section a) is impregnated at 25° C. by the dipping process and then dried in a circulating air oven for 18 minutes at 180° C. (resin content of the resulting prepregs 39% by weight). 10 layers of the impregnated fabric are then pressed hot between two 35 microns thick copper foils, which have been pre-treated by electrolytic surface-coating with brass. The press is initially kept under a light contact pressure for 2-3 minutes and the pressure is then increased to $392.28 \times 10^4$ Pa and the material is pressed for one hour at 180° C. The test pieces are then removed from the press and postcured for a further 6 hours in an oven at 240° C. (resin content of the resulting laminate sheets 35% by weight).

Properties of the copper-coated laminate sheets thus obtained:

Flexural strength in N/mm² according to ISO/R 178;
(a) initial value; (b) after aging for 10 days at 270° C.

Absorption of water in % by weight after 24 hours at 23° C. The measurements are carried out on flexural test pieces according to VSM Standard 77,103.

Dielectric loss factor tgδ/50 Hz according to DIN 53,483; (a) initial value measured at 23° C.; (b) after storing in boiling water for 6 hours.

Dielectric constant $\epsilon_r$/50 Hz according to DIN 53,483; (a) initial value measured at 23° C.; (b) after storing in boiling water for 6 hours.

ISO/R = International Standards Organisation/Recommendations; VSM = Verein Schweizerischer Maschinenindustrieller; DIN = Deutsche Industrie Norm.

The results are given in Table III below. Numbering of the test products and of the test pieces is the same as under (a).

TABLE III

| | Test product No. | | | | | | | | |
|---|---|---|---|---|---|---|---|---|---|
| | 1 | 2 | 3 | 4 | 5 | 6 | 7 | I | II |
| Flexural Strength N/mm² | | | | | | | | | |
| (a) Initial value | 422.3 | 401.0 | 586.7 | 553.2 | 427.2 | 465.0 | 429.1 | 402.0 | 453.6 |
| (b) After aging for 10 days at 270° C. | 282.4 | 108.8 | 162.8 | 220.3 | 224.5 | 239.4 | 353.8 | 349.9 | 318.4 |
| Absorption of water in % by weight after 24 hours at 23° C. | 0.54 | 0.28 | 0.29 | 0.23 | 0.24 | 0.26 | 0.25 | 0.27 | 0.13 |
| Dielectric loss factor tgδ/50 Hz | | | | | | | | | |
| (a) Initial value | 1.08 | 1.15 | 2.71 | 0.86 | 0.26 | 0.26 | 0.28 | 0.33 | 0.35 |
| (b) After storing in boiling water for 6 hours | 6.57 | 2.81 | 4.22 | 1.93 | 0.65 | 0.55 | 0.45 | 0.73 | 0.61 |
| Dielectric constant $\epsilon_r$/50 Hz | | | | | | | | | |
| (a) Initial value | 5.1 | 5.4 | 5.1 | 6.6 | 5.0 | 4.7 | 5.1 | 5.3 | 5.5 |
| (b) After storing in boiling water for 6 hours | 6.9 | 5.8 | 5.5 | 7.9 | 5.2 | 4.9 | 5.3 | 5.6 | 5.7 |

What is claimed is:

1. A compound of formula I

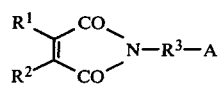

wherein A is a group $-C(R^4)=C(R^5)(R^6)$ or $-\equiv C-R^5$, $R^1$ and $R^2$ are each methyl, $R^3$ is a direct bond, straight-chain or branched-chain alkylene having 1-8 C atoms or cyclohexylene, $R^4$ and $R^6$ independently of one another are hydrogen, methyl or ethyl, and $R^5$ is hydrogen or alkyl having 1-9 C atoms.

2. A compound according to claim 1 which is

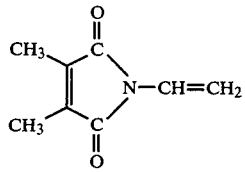

3. A compound according to claim 1 which is

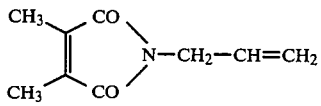

4. A compound of the formula I according to claim 1, in which A is $-C\equiv C-R^5$, $R^1$ and $R^2$ are each methyl, $R^3$ is methylene, isopropylidene, sec-amylidene or cyclohexylidene, and $R^5$ is hydrogen or methyl.

5. A compound according to claim 1 in which A is $-C(R^4)=C(R^5)(R^6)$, $R^1$ and $R^2$ are each methyl, $R^3$ is a direct bond or methylene, $R^4$ and $R^6$ independently of one another are hydrogen or methyl, and $R^5$ is hydrogen, methyl or n-octyl.

* * * * *

UNITED STATES PATENT AND TRADEMARK OFFICE
CERTIFICATE OF CORRECTION

PATENT NO. : 4,301,075
DATED      : NOVEMBER 17, 1981
INVENTOR(S): DIETER LOHMANN ET AL

It is certified that error appears in the above—identified patent and that said Letters Patent is hereby corrected as shown below:

Claim 1, Column 16, line 6 reads:

"wherein A is a group $-C(R^4)=C(R^5)(R^6)$ or $-\equiv C-R^5$,"

Should read:

-- wherein A is a group $-C(R^4)=C(R^5)(R^6)$ or $-C\equiv C-R^5$, --

Signed and Sealed this

Tenth Day of August 1982

[SEAL]

*Attest:*

*Attesting Officer*

GERALD J. MOSSINGHOFF

*Commissioner of Patents and Trademarks*